(12) United States Patent
Arad (Abboud)

(10) Patent No.: US 7,907,998 B2
(45) Date of Patent: Mar. 15, 2011

(54) BIO-IMPEDANCE APPARATUS AND METHOD

(75) Inventor: Shimon Arad (Abboud), Tel-Aviv (IL)

(73) Assignee: Tel Aviv University Future Technology Development L.P., Tel Aviv (IL)

( * ) Notice: Subject to any disclaimer, the term of this patent is extended or adjusted under 35 U.S.C. 154(b) by 707 days.

(21) Appl. No.: 11/225,630

(22) Filed: Sep. 13, 2005

(65) Prior Publication Data

US 2006/0064029 A1    Mar. 23, 2006

Related U.S. Application Data

(63) Continuation-in-part of application No. 11/023,912, filed on Dec. 27, 2004, which is a continuation-in-part of application No. 10/189,161, filed on Jul. 3, 2002, now Pat. No. 7,096,061.

(51) Int. Cl.
*A61B 5/02* (2006.01)
*A61B 5/08* (2006.01)
*A61B 5/05* (2006.01)
*A61B 5/00* (2006.01)
*A61B 18/04* (2006.01)

(52) U.S. Cl. ......... 600/547; 600/481; 600/484; 600/506; 600/533; 600/561; 606/32

(58) Field of Classification Search ............. 600/481, 600/484, 506, 533, 547, 561, 584; 606/32; 607/17
See application file for complete search history.

(56) References Cited

U.S. PATENT DOCUMENTS

| | | | |
|---|---|---|---|
| 5,178,154 A * | 1/1993 | Ackmann et al. ............ 600/526 |
| 5,311,878 A * | 5/1994 | Brown et al. ............... 600/547 |
| 5,746,214 A | 5/1998 | Brown et al. |
| 5,749,369 A | 5/1998 | Rabinovich et al. |
| 5,788,643 A | 8/1998 | Feldman |
| 6,134,472 A | 10/2000 | Strandberg et al. |
| 6,135,105 A * | 10/2000 | Lampotang et al. ..... 128/204.21 |
| 6,224,553 B1 | 5/2001 | Nevo |
| 6,256,368 B1 | 7/2001 | Hsich et al. |
| 6,387,671 B1 | 5/2002 | Runinsky et al. |
| 6,473,640 B1 * | 10/2002 | Erlebacher ................. 600/547 |
| 6,517,488 B1 | 2/2003 | Hossack |
| 6,647,289 B2 | 11/2003 | Prutchi |
| 7,096,061 B2 | 8/2006 | Arad |

(Continued)

FOREIGN PATENT DOCUMENTS

EP     0669822     9/1995

(Continued)

OTHER PUBLICATIONS

Belalcazar et al. "Improved Lung Edema Monitoring with Coronary Vein Pacing Leads: A Simulation Study", Physiological Measurement. 25: 457-487, 2004.

(Continued)

*Primary Examiner* — Max Hindenburg
*Assistant Examiner* — Sean P Dougherty

(57) ABSTRACT

A method of determining an impedance of at least one lung of a patient having an implanted pacemaker that comprises first and second leads and a case, the method comprising:

a) using the leads and the case to acquire at least a first and a second impedance measurement responsive to impedance of the patient's chest that are at least partially independent; and b) using the impedance measurements to determine the impedance of at least one of the lungs substantially independently of impedance of the other lung.

21 Claims, 7 Drawing Sheets

U.S. PATENT DOCUMENTS

| | | | |
|---|---|---|---|
| 7,149,573 B2* | 12/2006 | Wang | 600/547 |
| 7,184,821 B2* | 2/2007 | Belalcazar et al. | 600/547 |
| 2002/0123674 A1* | 9/2002 | Plicchi et al. | 600/300 |
| 2003/0216630 A1 | 11/2003 | Jersey-Willuhn et al. | |
| 2004/0006279 A1 | 1/2004 | Arad (Abboud) | |
| 2004/0102712 A1 | 5/2004 | Belalcazar et al. | |
| 2004/0116819 A1 | 6/2004 | Alt | |
| 2004/0215097 A1* | 10/2004 | Wang | 600/547 |
| 2004/0220637 A1* | 11/2004 | Zdeblick et al. | 607/17 |
| 2005/0080460 A1 | 4/2005 | Wang et al. | |
| 2005/0107719 A1 | 5/2005 | Arad (Abbound) | |
| 2005/0124908 A1* | 6/2005 | Belalcazar et al. | 600/547 |

FOREIGN PATENT DOCUMENTS

| | | |
|---|---|---|
| EP | 0533732 | 12/1995 |
| EP | 1238630 | 9/2002 |
| GB | 2 138 148 | 10/1984 |
| GB | 2138148 | 10/1984 |
| GB | 2315332 | 1/1998 |
| JP | 05-507864 | 11/1993 |
| JP | 08-502430 | 3/1996 |
| WO | WO 98/33553 | 8/1998 |
| WO | WO 2004/004539 | 1/2004 |
| WO | WO 2007/031951 | 3/2007 |

OTHER PUBLICATIONS

Dong et al. "GVSPM for Reconstruction in Electrical Impedance Tomography", IEEE Transactions on Magnetics, 39(3): 1630-1633, 2003.

Fang et al. "Finite Difference, Finite Element and Finite Volume Methods Applied to Two-Point Boundary Value Problems", Journal of Computational and Applied Mathematics, 139: 9-19, 2002.

Greenberg et al "Reproducibility of Impedance Cardiography Hemodynamic Measures in Clinically Stable Heart Failure Patients", ICG Reproducibility in Heart Failure, p. 1-7, 2000.

Jithesh et al. "A Review on Computational EMI Modeling Techniques", Proceedings of INCEMIC, p. 159-166, 2003.

Lee et al. "Three-Dimensional Forward Solver and Its Performance Analysis for Magnetic Resonance Electrical Impedance Tomography (MREIT) Using Recessed Electrodes", Physics in Medicine and Biology, 48: 1971-1986, 2003.

Li et al. "The Finite Volume Method and Application in Combinations", Journal of Computational and Applied Mathematics, 106: 21-53, 1999.

Matiussi "An Analysis of Finite Volume, Finite Element, and Finite Difference Methods Using Some Concepts From Algebraic Topology", Journal of Computational Physics, 133: 289-309, 1997.

Nakajima et al. "Comparison of Finite Element and Finite Volume Methods for Imcompressible Viscous Flows", AIAA Journal, Technical Notes, 32(5): 1090-1093.

Ollikainen et al. "Effects of Local Skull Inhomogeneities on EEG Source Estimation", Medical Engineering & Physics, 21: 143-154, 1999.

Pruis et al. "A Comparison of Different Numerical Methods for Solving the Forward Problem in EEG and MEG", Physiological Measurements, 14: Al-A9, 1993.

Scott et al. "Theoretical Model of Electrode Polarization and AC Electroosmotic Fluid Flow in Planar Electrode Arrays", Journal of Colloid and Interface Science, 238: 449-451, 2001.

Zlochiver et al. "Induced-Current Electrical Impedance Tomography: A2-D Theoretical Simulation", IEEE Transactions On Medical Imagining, 22(12), 1550-1560, 2003.

Abboud, S. et al.; "Numerical Calculation of the Potential Distribution Due to Dipole Sources in a Spherical Model of the Head;" 1994; Computers and Biomedical Research; vol. 27; pp. 441-455.

Barber, D. C.; "A Review of Image Reconstruction Techniques for Electrical Impedance Tomography;" Mar./Apr. 1989; Med. Phys.; vol. 16, No. 2; pp. 162-169.

Charach, G. et al.; "Transthoracic Monitoring of the Impedance of the Right Lung in Patients with Cardiogenic Pulmonary Edema;" Year 2001; Crit. Care Med.; vol. 29, No. 6; pp. 1137-1144.

Dodge, H. T. et al.; "Quantitative Contrast Angiography for Assessment of Ventricular Performance in Heart Disease"; Year 1983; J. Amm Coll Cardiol; pp. 73-81.

Dong, G. et al.; "Derivation from Current Density Distribution to Conductivities Based on the Adjoint Field Theory and Numerical Test With Finite Volume Method"; The 2nd Japan, Australia and New Zealand Joint Seminar, Jan. 24-25, 2002, Kanazawa, Japan Applications of ElectroMagnetic Phenomena in Electrical and Mechanical Systems; 8 pages.

Edwardson, M. et al.; "A Bioelectrical Impedance Analysis Device for Improved Management of Congestive Heart Failure;" Year 2000; Computers in Cardiology; vol. 27; pp. 9-12.

Eyuboglu, B. M. et al.; "In Vivo Imaging of Cardiac Related Impedance Changes;" Mar. 1989; IEEE Engineering in Medicine and Biology Magazine; vol. 8, No. 1; pp. 39-45; XP 000002279.

Govreen-Segal, D. et al.; "Real-Time PC-Based System for Dynamic Beat-to-Beat QT-RR Analysis;" Year 1999; Computers and Biomedical Research; vol. 32; pp. 336-354.

Hoetnik, A. E. et al.; "Comparing Spot Electrode Arrangements for Electric Impedance Cardiography"; Physiol. Meas. 23 (2002); Apr. 8, 2002; pp. 457-467.

Imhoff, M. et al.; "Noninvasive Whole-Body Electrical Bioimpedance Cardiac Output and Invasive Thermodilution Cardiac Output in High-Risk Surgical Patients"; Crit Care Med 2000, vol. 28, No. 8; Copyright 2000: pp. 2812-2818.

Lucquin, B. et al.; "Finite Differences in Time and Finite Volumes in Space;" Year 1998; Introduction to Scientific Computing; Section 7.8; John Wiley & Sons; pp. 300-304.

Newell, J. C. et al.; "Assessment of Acute Pulmonary Edema in Dogs by Electrical Impedance Imaging"; Feb. 1996; IEEE Transactions on Biomedical Engineering; vol. 43, No. 2; pp. 133-138.

Raajmakers, E. et al.; "The Influence of Extravascular Lung Water on Cardiac Output Measurements Using Thoracic Impedance Cardiography"; Physiol. Meas. 19 (1998); Aug. 27, 1998; pp. 491-499.

Record, P. M. et al.; "Multifrequency Electrical Impedance Tomography;" Year 1992; 11815 Clinical Physics and Physiological Measurement; vol. 13, Supplement A; pp. 67-72.

Riu, P. et al.; "In Vivo Static Imaging for the Real and the Reactive Parts in Electrical Impedance Tomography Using Multifrequency Techniques;" Oct. 29, 1992; IEEE; pp. 1706-1707; XP 000514393.

Rosenfeld, M. et al.; "Numerical Solution of the Potential Due to Dipole Sources in Volume Conductors With Arbitrary Geometry and Conductivity;" Jul. 1996; IEEE Transactions on Biomedical Egineering; vol. 43, No. 7; pp. 679-689.

Shahidi, A. V. et al.; "Impedance Tomography: Computational Analysis Based on Finite Element Models of a Cylinder and a Human Thorax;" Year 1995; Annals of Biomedical Engineering; vol. 23; pp. 61-69.

Subramanyan, R. et al.; "Total Body Water in Congestive Heart Failure—A Pre and Post Treatment Study;" Sep. 1980; Jour. Asso. Phys. Ind.; vol. 28; pp. 257-262.

Versteeg, H. K. et al.; "An Introduction to Computational Fluid Dynamics—The Finite Volume Method", Chapter 2 "Conservation Laws of Fluid Motion and Bonundary Conditions"; Longman Scientific & Technical, 1995; pp. 10-40.

Official Action Dated Nov. 16, 2009 From the US Patent and Trademark Office Re.: U.S. Appl. No. 11/023,912.

Official Action Dated Aug. 31, 2004 From the US Patent and Trademark Office Re.: U.S. Appl. No. 10/189,161.

Noordegraaf et al. "Pulmonary Perfusion Measured by Means of Electrical Impedance Tomography", Physiological Measurement, XP020073840, 19(2):263-273, May 1, 1998.

Official Action Dated Apr. 20, 2010 From the US Patent and Trademark Office Re.: U.S. Appl. No. 11/023,912.

Official Action Dated Jan. 27, 2009 From the US Patent and Trademark Office Re.: U.S. Appl. No. 11/023,912.

Communication Pursuant to Article 94(3) EPC Dated Jul. 1, 2009 From the European Patent Office Re.: Application No. 03735951.0.

International Search Report Dated May 25, 2004 From the International Searching Authority Re.: Application No. PCT/IL03/00556.

Notification of Reasons of Rejection Dated Jul. 13, 2009 From the Japanese Patent Office Re.: Application No. 2004-519141 and Its Translation Into English.

Notification of Reasons of Rejection Dated Feb. 16, 2010 From the Japanese Patent Office Re.: Application No. 2004-519141 and Its Translation Into English.

Official Action Dated Jul. 13, 2007 From the US Patent and Trademark Office Re.: U.S. Appl. No. 11/023,912.

Official Action Dated Jan. 15, 2010 From the US Patent and Trademark Office Re.: U.S. Appl. No. 11/225,630.

Response Dated Dec. 2, 2009 to Official Action of Jun. 2, 2009 From the US Patent and Trademark Office Re.: U.S. Appl. No. 11/225,630.

Response Dated Jan. 3, 2010 to Communication Pursuant to Article 94(3) EPC of Jul. 10, 2009 From the European Patent Office Re.: Application No. 03735951.0.

Response Dated Jan. 6, 2010 to Notification of Reasons for Rejection of Jul. 13, 2009 From the Japanese Patent Office Re.: Application No. 2004-519141.

Response Dated Mar. 16, 2010 to Official Action of Nov. 16, 2009 From the US Patent and Trademark Office Re.: U.S. Appl. No. 11/023,912.

Tang et al. "Effects of Incompatible Boundary Information in EIT on the Convergence Behavior of An Iterative Algorithm", IEEE Transactions on Medical Imaging, 21(6): 620-628, Jun. 2002.

Response Dated Apr. 28, 2010 to Notification of Reasons of Rejection of Feb. 16, 2010 From the Japanese Patent Office Re.: Application No. 2004-519141.

Official Action Dated Oct. 13, 2010 From the US Patent and Trademark Office Re.: U.S. Appl. No. 11/023,912.

Official Action Dated Jan. 28, 2009 From the US Patent and Trademark Office Re.: U.S. Appl. No. 11/225,630.

Abboud et al. "Numerical Calculation of the Potential Distribution Due to Dipole Sources in A Spherical Model of the Head", Computers and Biomedical Research, 27: 441-455, 1994.

Barber "A Review of Image Reconstruction Techniques for Electrical Impedance Tomography", Medical Physics, 16(2): 162-169, 1989.

Belalcazar et al. "Improved Lung Edema Monitoring With coronary Vein Pacing Leads: A Simulation Study", Physiological Measurement, Institute of Physics Publishing, 25(2): 475-487, 2004. § [04.3], [04.5], [04.6], Figs.5, 7, Table 4.

Charach et al. "Transthoracic Monitoring of the Impedance of the Right Lung in Patients With Cardiogenic Pulmonary Edema", Critical Care Medicine, 29(6): 1137-1144, 2001.

Dodge et al. "Quantitative Contrast Angiography for Assessment of Ventricular Performance in Heart Disease", Journal of the American College of Cardiology, p.73-81, 1983. Abstract.

Dong et al. "Derivation From Current Density Distribution to Conductivities Based on the Adjoint Field Theory and Numerical Test With Finite Volume Method", Proceedings of the 2nd Japan-Australia-New Zealand Joint Seminar on Applications on Electromagnetic Phenomena in Electrical and Mechanical Systems, Kanazawa, Japan, XP002515750, p.89-96, Jan. 24, 2002. Reetrieved From the Internet: <URL:http://www.ysaitoh.k.hosei.ac.jp/labor/ysaitoh/papers/Conference/2003JSAE_M_2ndJANS_Derivation_fromCurrent_Density_Distribution_to_Conductivities_based_on_the_Adjoin_Field_Theory_and_Numerical_Test_with_Finite_Volume_Met hod.pdf>. Introduction: p. 89, Part 3.1: p. 91-92.

Edwardson et al. "A Bioelectrical Impedance Analysis Device for Improved Management of Congestive Heart Failure", Computers in Cardiology, 27: 9-12, 2000.

Eyüboğlu et al. "In Vivo Imaging of Cardiac Related Impedance Changes", IEEE Engineering in Medicine & Biology Magazine, 8(1): 39-45, 1989.

Govreen-Segal et al. "Real-Time PC-Based System for Dynamic Beat-to-Beat QT-RR Analysis", Computers and Biomedical Research, 32: 336-354, 1999.

Griffiths "Tissue Spectroscopy With Electrical Impedance Tomography: Computer Simulations", IEEE Transactions on Biomedical Engineering, XP002515753, 42(9): 948-954, Sep. 1995. Part III. B Numerical Model.

Hoetnik et al. "Comparing Spot Electrode Arrangements for Electric Impedance Cardiography", Physiological Measurement, 23: 457-467, 2002. Abstract.

Imhoff et al. "Noninvasive Whole-Body Electrical Bioimpedance Cardiac Output and Invasive Thermodilution Cardiac Output in High-Risk Surgical Patients", Critical Care Medicine, 28(8): 2812-2818, 2000. Abstract.

Li "Multifrequente Impedanztomographie zur Darstellung der elektrischen Impedanzverteilung im menschlichen Thorax", Dissertation, Institut für Biomedizinische Technik, Stuttgart, Deutsche Nationalbibliothek, XP002515749, Feb. 7, 2007. Retrieved From the Internet: <URL:http://deposit.ddb.de/cgi-bin/dokserv?idn=960463143>. Abstract: p.13-22, Part 2: p.31-49, Part 3.2: p.60-63, Part 4.1: p.87-89, Part 6: p.135-157, Figs.4.1, 4.2, 6.1, 6.9, 6.10.

Lucquin et al. "Finite Differences in Time and Finite Volumes in Space", Introduction to Scientific Computing, XVII(Sec.7.8): 300-304, 1998.

Newell et al. "Assessment of Acute Pulmonary Edema in Dogs by Electrical Impedance Imaging", IEEE Transactions on Biomedical Engineering, 43(2): 133-138, 1996.

Raaijmakers et al. "The Influence of Extravascular Lung Water on Cardiac Output Measurements Using Thoracic Impedance Cardiography", Physiological Measurement, 19: 491-499, 1998. Abstract.

Record et al. "Multifrequency Electrical Impedance Tomography", Clinical Physics and Physiological Measurement, 13(Suppl.A): 67-72, 1992.

Riu et al. "In Vivo Static Imaging for the Real and the Reactive Parts in Electrical Impedance Tomography Using Multifrequency Techniques", IEEE, p.1706-1707, 1992.

Rosenfeld et al. "Numerical Solution of the Potential Due to Dipole Sources in Volume Conductors With Arbitrary Geometry and Conductivity" IEEE Transactions on Biomedical Engineering, XP002515751, 43(7): 679-689, Jul. 1996.

Shahidi et al. "Impedance Tomography: Computational Analysis Based on Finite Element Models of A Cylinder and A Human Thorax", Annals of Biomedical Engineering, 23: 61-69, 1995.

Subramanyan et al. "Total Body Water in Congestive Heart Failure - A Pre and Post Treatment Study", Journal of the Association of Physicians in India, 28: 257- 262, 1980.

Versteeg et al. "Conservation Laws of Fluid Motion and Boundary Conditions", An Introduction to Computational Fluid Dynamics - The Finite Volume Method, Longman Scientific & Technical, Chap. 2: 10-40, 1995. Only Description and Table of Contents, Article Not Available!.

Watkins "Orthogonal Matrices and the Least-Squares Problem", Fundamentals of Matrix Computations, Wiley-Interscience, Chap.3: 134-157, 2002.

International Preliminary Examination Report Dated May 18, 2006 From the International Preliminary Examining Authority Re.: Application No. PCT/IL03/00556.

International Search Report Dated Aug. 2, 2007 From the International Searching Authority Re.: Application No. PCT/IB2006/053263.

Notice of Allowance Dated Apr. 6, 2006 From the US Patent and Trademark Office Re.: U.S. Appl. No. 10/189,161.

Official Action Dated Dec. 6, 2005 From the US Patent and Trademark Office Re.: U.S. Appl. No. 10/189,161.

Office Action Dated Mar. 23, 2005 From the US Patent and Trademark Office Re.: U.S. Appl. No. 10/189,161.

Response Dated Sep. 14, 2010 to Official Action of Apr. 20, 2010 From the US Patent and Trademark Office Re.: U.S. Appl. No. 11/023,912.

Supplementary European Search Report Dated Mar. 4, 2009 From the European Patent Office Re.: Application No. 03735951.0.

Written Opinion Dated Aug. 2, 2007 From the International Searching Authority Re.: Application No. PCT/IB2006/053263.

Written Opinion Dated Apr. 22, 2005 From the International Preliminary Examining Authority Re.: Application No. PCT/IL03/00556.

Dehghani et al. "Incorporating A Priori Anatomical Information Into Image Reconstruction in Electrical Impedance Tomography", Physiological Measurement, XP020073872, 20(1): 87-102, Feb. 1, 1999. Abstract.

Glidewell et al. "Anatomically Constrained Electrical Impedance Tomography for Anisotropic Bodies Via A Two-Step Approach", IEEE Transactions on Medical Imaging, XP002515752, 14(3): 498-503, Sep. 1995. Abstract, Part I. Introduction, Part II.B Inverse Problem, Part IV. Step One, Part V. Step Two.

Noble et al. "Monitoring Patients With Left Ventricular Failure by Electrical Impedance Tomography", The European Journal of Heart Failure, XP002515754, 1(4): 379-384, Dec. 1999. Abstract.

Newell et al. "Phasic Three-Dimensional Impedance Imgaging of Cardiac Activity", Physiological Measurement, 23: 203-209, 2002.

Zlochiver et al. "Parametric EIT for Monitoring Cardiac Stroke Volume", Physiological Measurement, 27: S139-S146, 2006.

* cited by examiner

BIO-IMPEDANCE APPARATUS AND METHOD

RELATED APPLICATIONS

This application is a continuation-in-part of U.S. application Ser. No. 11/023,912 (publication No. 2005/0107719-A1), filed on Dec. 27, 2004, which is a continuation-in-part of U.S. application Ser. No. 10/189,161 (publication No. 2004/0006279-A 1), filed on Jul. 3, 2002.

FIELD OF THE INVENTION

The field of the invention relates to bio-impedance measurements of the chest, particularly for monitoring the lungs and heart of a patient.

BACKGROUND OF THE INVENTION

Patients suffering from CHF, and other conditions that cause pulmonary edema, are typically treated with diuretic drugs to reduce the fluid in their lungs. But these drugs can also cause kidney damage and other medical problems, so it is generally advantageous, in treating these patients, to monitor the level of pulmonary edema, in order to maintain an optimized treatment regime. Levels of pulmonary edema may be designated by a scale that ranges from the least severe cases to the most severe. Bio-impedance techniques offer a non-invasive and inexpensive method for monitoring fluid volume in the lungs.

Systems for bio-impedance monitoring of pulmonary edema, developed in the 1970s, are described by R. N. McCarthy and D. Dosh, "Assessment of pulmonary edema in acute congestive heart failure with impedance cardiography," *J. Am. Osteo. Assoc.* 74, 879 (1975), and by M. R. Khan et al, "Quantitative electrical-impedance plethysomography for pulmonary oedema," *Med. Bio. Eng. Comp.* 15, 627-633 (1977). These systems used two or four electrodes placed on the outside of the body at the upper and lower ends of the thorax. A commercially available system similar to these, the BioZ system sold by Cardiodynamics, is described by B. H. Greenberg et al, "Reproducibility of impedance cardiography hemodynamic measures in clinically stable heart failure patients," *CHF* 6, 19-26 (2000). The systems described in the above referenced documents generally yield only an estimate of the average overall thorax impedance, which can be influenced by factors, for example the thickness of surrounding fat layers, other than pulmonary edema.

Another kind of bio-impedance system for lung monitoring is usable only for patients who have implanted pacemakers or defibrillators having electrical leads permanently placed inside the heart, typically in the right atrium and the right ventricle. One such system, the Insync Sentry, made by Medtronic, is described by L. Wang et al, "Prediction of CHF hospitalization by ambulatory intrathoracic impedance measurement in CHF patients is feasible using pacemaker or ICD lead systems," *PACE* 26, 959 (2003). In this system, current is injected between the right ventricle lead and the case of the pacemaker or defibrillator, and the impedance between these two points is measured. This impedance is found to be well correlated with the overall amount of fluid in the lungs, and is insensitive to external factors such as the thickness of fat layers surrounding the thorax.

A. Belalcazar and R. P. Patterson, "Improved lung edema monitoring with coronary vein pacing leads: a simulation study," *Physiol. Meas.* 25, 475-487 (2004), describes a bio-impedance system using a new type of implanted pacemaker or defibrillator. The new pacemaker or defibrillator has a lead in the left ventricle coronary vein for improved pacemaking or defibrillating functioning, in addition to leads in the right atrium and right ventricle. Like many pacemakers and defibrillators, the described pacemaker or defibrillator has its case implanted in the left pre-pectoral position. Measuring impedance between each of these leads and the case allows changes in impedance due to pulmonary edema to be evaluated independently of changes in impedance due to intravascular fluid. The left ventricle coronary vein lead is said by Belalcazar and Patterson to be important for monitoring edema, because impedance measurements using this lead are more sensitive to pulmonary edema, and less sensitive to the volume of intravascular fluid, than impedance measurements using the right atrium and right ventricle leads.

Impedance measurements using any of the leads in the devices described by Belalcazar and Patterson are said to be sensitive only to left lung edema, not to right lung edema, in patients where the degree of edema is very different in the two lungs (unilateral edema). Whereas it is pointed out that for most pulmonary edema patients, fluid is distributed approximately uniformly in both lungs, pulmonary edema concentrated asymmetrically in the right lung does occur and can be a symptom of mitral regurgitation. The authors state that, for detecting pulmonary edema, "The right lung can only be monitored with a right pectoral implant."

Ziochiver, Rosenfeld and Abboud, in "Induced Current Electrical Impedance Tomography: A 2-D Theoretical Simulation," *IEEE Transactions on Medical Imaging* 22, 1550-1560 (2003), describe an impedance imaging system in which eight or more electrodes are arranged around the outside of the chest. Impedances are measured between different pairs of the electrodes, and the measurements are used to calculate an impedance image of the chest, with sufficiently high resolution to "see" each of the two lungs and the heart. Abboud is also an inventor on published U.S. application 2004/0006279-A1, which describes a similar system, and on the present application.

The disclosures of all the patents and publications mentioned above are incorporated herein by reference.

SUMMARY OF THE INVENTION

An aspect of some embodiments of the invention relates to determining impedance of each of a patient's lungs responsive to at least two impedance measurements, acquired using first and second electrical leads of an implanted pacemaker. In some embodiments of the invention, a defibrillator is used instead of a pacemaker, or a combined unit is used which acts both as a pacemaker and a defibrillator. It should be understood that, whenever a pacemaker is mentioned, a defibrillator or combined unit may be used instead.

An aspect of some embodiments of the invention, relates to providing relatively accurate determinations of impedance of a lung of a patient responsive to the at least two impedance measurements.

According to an aspect of some embodiments of the invention, the at least two impedance measurements put at least two constraints on solutions to Poisson's equation, in a model of the chest in which the impedances of the two lungs are treated as independent variables. The impedance of a given lung is found for which the solution to Poisson's equation satisfies the constraints.

In an embodiment of the invention, current is generated between the first lead and the case, and voltage is measured between the first lead and the case to make a first impedance measurement of the at least two impedance measurements.

Voltage is measured between the second lead and the case to make the second impedance measurement. In another embodiment of the invention, current is generated between the second lead and the case to make the second impedance measurement. In other embodiments of the invention, to make one or more of the impedance measurements, current is generated between each of the leads and the case, with a known current passing through each of the leads, or a known relationship between the currents that are passed through the leads. In some embodiments of the invention, to make one or more of the at least two impedance measurements, the measured voltage is a combination, for example a particular weighted average, of the potential differences between each of the leads and the case.

By using different configurations of the two leads when making voltage measurements and/or when generating currents, as described above by ways of example, different impedance measurements involve currents that are distributed differently in the chest and/or voltages between different parts of the chest. The different impedance measurements will therefore generally have different dependences on the impedances of the left and right lungs. The different impedance measurements define a set of two independent constraints on a solution to a Poisson equation for the chest. A lung impedance for either of the lungs or both of the lungs is determined responsive to a solution of the equation that satisfies the constraints.

The inventors have determined that in general, requiring a solution to Poisson's equation to satisfy at least two independent conditions, corresponding to at least two impedance measurements acquired using electrodes of an implanted device, provides estimates of lung impedance that are more accurate than estimates provided by prior art methods using implanted devices.

Optionally, the first and second leads are located in the right atrium and the right ventricle, as in a traditional pacemaker. Optionally, the case is implanted in the traditional left pre-pectoral position. Alternatively, one of the leads is optionally located in the left ventricle coronary vein, and/or the case is implanted in the right pre-pectoral position, as in some new pacemakers.

The invention may thus be used in patients implanted with any of a variety of pacemaker types and configurations, rather than being limited to a particular configuration or type. Furthermore, by making use of the different dependences of impedance measurements on left and right lung impedance, the right lung impedance, for example, may be found even if both impedance measurements are more sensitive to the left lung impedance, which is often the situation when a pacemaker is implanted on the left side of the chest.

An aspect of an embodiment of the invention relates to determining lung impedance at least in part from an impedance measurement that is a ratio of voltage between one lead of an implanted pacemaker and its case, and a current generated at least partly between the other lead and the case.

It should be understood that, rather than making impedance measurements, and solving equations involving the impedance measurements to find the lung impedances, as described above, optionally voltage and current measurements used to determine the impedance measurements are used directly in equations that are solved to find the lung impedances. As used herein, "making impedance measurements" includes measuring any quantities, such as voltage and current, which could be used to determine an impedance measurement, even if the impedance measurement is not explicitly calculated.

Pulmonary edema is primarily a condition of excess extracellular fluid in the lungs. For frequencies below 100 kHz, bio-impedance measurements in general depend substantially on impedance of extracellular fluid, which is resistive, and are substantially independent of impedance of intracellular fluid which is substantially reactive. For frequencies below about 100 kHz, intracellular current does not substantially contribute to total current between electrodes used to measure impedance, since for these relatively low frequencies current does not easily cross the cell membranes. Generally, frequencies below 100 kHz are used for purposes of monitoring pulmonary edema, and the lung impedances as well as the measured impedances are predominantly resistive. At higher frequencies, body impedance depends also on intracellular fluid and generally has a substantial reactive part, since the cell membranes act like capacitors and contribute displacement current to total current between electrodes used to measure impedance. For some medical conditions, which involve abnormal levels of intracellular fluid, it may be advantageous to determine impedance in accordance with an embodiment of the invention at frequencies above 100 kHz, and to determine both the resistive and reactive part of the lung impedances.

As used herein, "lung impedance" means the specific impedance of the lung, a a bulk property of the lung tissue, which includes the specific resistance (resistivity) of the lung tissue, and may also include a reactive part.

Optionally, values for the left and right lung impedances, consistent with the impedance measurements, are found iteratively by first estimating impedances for the left and right lungs. Expected voltages between each of the two leads and the pacemaker or defibrillator case for given currents are then determined responsive to the estimated lung impedances. The expected voltages are compared to the measured voltages at the two leads. Differences between the expected and measured voltages are used to produce new estimates for the left and right lung impedances, using for example a Newton-Raphson method, or a modified Newton-Raphson method. The procedure is iterated until a convergence criterion is satisfied.

There is thus provided, according to an exemplary embodiment of the invention, a method of determining an impedance of at least one lung of a patient having an implanted pacemaker that comprises first and second leads and a case, the method comprising:
 a) using the leads and the case to acquire at least a first and a second impedance measurement responsive to impedance of the patient's chest that are at least partially independent; and
 b) using the impedance measurements to determine the impedance of at least one of the lungs substantially independently of impedance of the other lung.

Optionally, using the measurements to determine the impedance of at least one of the lungs comprises determining the impedance of said lung such that Poisson's equation for a model of the chest has a solution consistent with the at least two impedance measurements.

Optionally, the model of the chest treats the impedances of the two lungs as two independent variables.

Optionally, acquiring the impedance measurements comprises, for each impedance measurement:
 a) generating a current between at least one of the leads and the case; and
 b) measuring a voltage involving a potential difference between at least one of the leads and the case;
wherein, for each impedance measurement, a different configuration of the first and second leads is used than is used for any other of the impedance measurements, for generating the current or for measuring the voltage or for both.

Optionally, for the first and second impedance measurements, the current is generated only between the case and one of the leads, the same lead for both the first and second impedance measurements, and the voltage involves only a potential difference between the case and one of the leads, a different one for the first impedance measurement than for the second impedance measurement.

Optionally, determining the impedance of at least one lung comprises determining the impedances of both lungs.

Optionally, the impedance measurements also comprise a third impedance measurement.

In an embodiment of the invention, the method also includes determining a third parameter of the thorax, in addition to the two lung impedances.

Optionally, the third parameter comprises an intravascular volume of the thorax.

Alternatively, at least one of the lung impedances pertains only to a portion of said lung, and the third parameter comprises an impedance of another portion of said lung.

Optionally, a least squares method is used to find a fit of the two lung impedances to the at least three impedance measurements.

In an embodiment of the invention, determining the lung impedances comprises:
a) making an initial guess for the values of the lung impedances;
b) calculating the expected impedance measurements for said values of the lung impedances;
c) correcting the values of the impedances according to a difference between the measured and expected values for the impedance measurements; and
d) repeating (b) and (c) until a convergence criterion is satisfied.

Optionally, calculating the expected impedance measurements comprises using one or more of the finite element method, the finite difference method, the finite boundary element method, and the finite volume method.

Optionally, one of the leads is implanted in the right ventricle.

Optionally, one of the leads is implanted in the right atrium.

Optionally, one of the leads is implanted in the left ventricle coronary vein.

Optionally, the case is implanted in the left pre-pectoral position.

Alternatively, the case is implanted in the right pre-pectoral position.

There is further provided, in accordance with an exemplary embodiment of the invention, a method of determining the impedance of at least one lung, comprising:
a) generating a first current between a pacemaker case implanted in the chest, and at least one of a first lead and a second lead implanted at different locations in the heart;
b) measuring a first voltage involving a potential difference between at least one of the leads and the case, due at least in part to at least a portion of the current which is generated between the other lead and the case; and
c) calculating the impedance of at least one lung from the first current and the first voltage.

There is further provided, in accordance with an exemplary embodiment of the invention, a pacemaker for bio-impedance measurements, comprising:
a) a case adapted for implanting in the chest;
b) a first lead adapted for implanting at a location in the heart;
c) a second lead adapted for implanting at a different location in the heart;
d) a bio-impedance system, adapted to make impedance measurements comprising at least a first and a second impedance measurement, using the case and the first and second leads; and
e) a data analyzer, adapted to determine an impedance of at least one of the lungs, substantially independently of impedance of the other lung.

BRIEF DESCRIPTIONS OF THE DRAWINGS

Exemplary embodiments of the invention are described in the following sections with reference to the drawings listed. The drawings are not necessarily to scale and the same reference numbers are generally used for the same or similar features that are shown on different drawings.

DETAILED DESCRIPTION OF EXEMPLARY EMBODIMENTS

Figure 1:
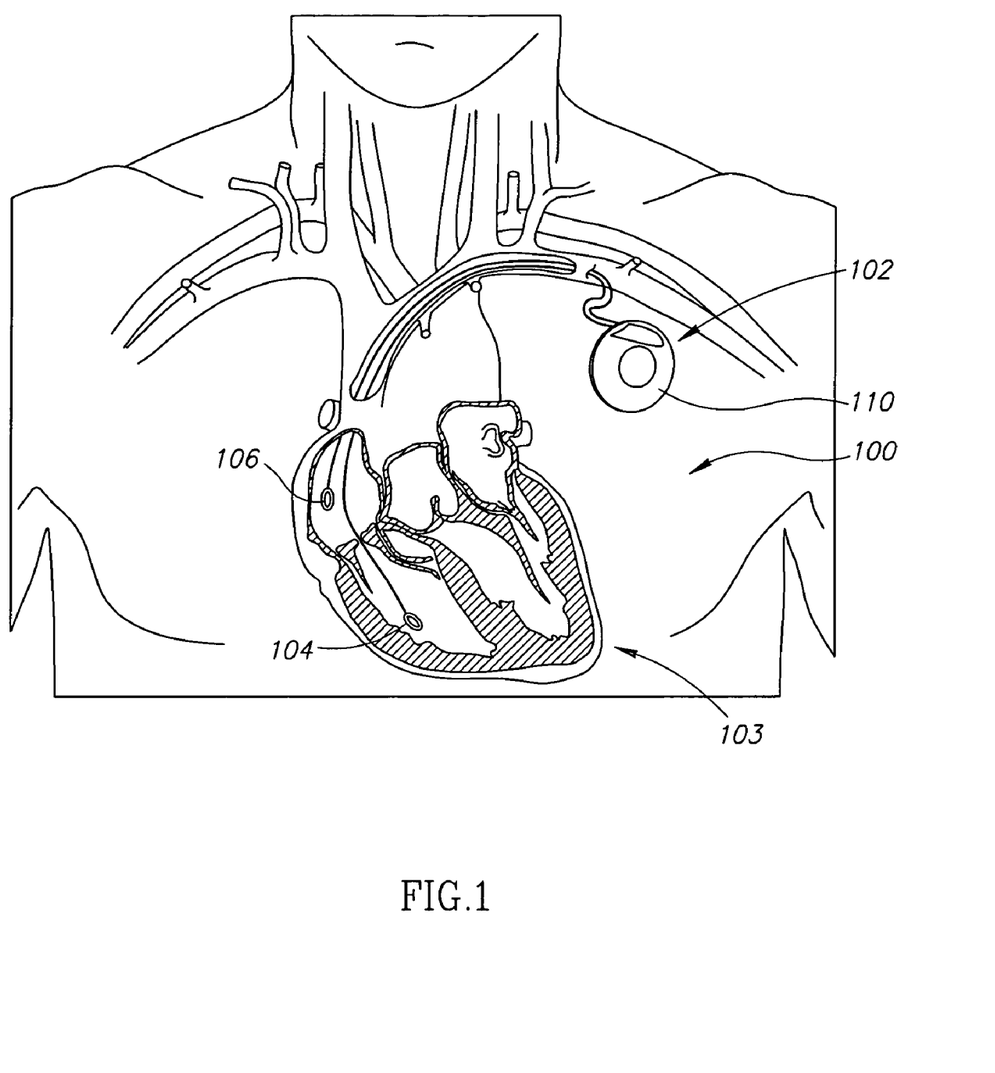
FIG. 1 is a schematic see-through view of a patient's chest, showing an implanted pacemaker with leads in the right atrium and ventricle.

FIG. 1 shows the chest 100 of a patient, with a pacemaker 102, implanted in the left pre-pectoral position. Pacemaker 102 has two leads, threaded through a vein to the heart 103. A lead 104 terminates in the right ventricle, and a lead 106 terminates in the right atrium. One of the leads is optionally in a different location, for example in the left ventricle coronary vein, or there are one or more additional leads in different locations. Pacemaker 102 applies changes in voltage periodically to the leads, resulting in current flowing through the leads, in order to reinforce the natural cardiac rhythm in the patient. In addition, in its role as a bio-impedance monitor, pacemaker 102 generates current from lead 104, lead 106, or both, through chest 100 and back to a case 110 that houses the pacemaker, and measures a resulting voltage difference or differences between the case and lead 104, lead 106, or both, in order to acquire bio-impedance measurements. Preferably case 110 comprises a conductor, at least in part, that is in good electrical contact with the tissue of the thorax, so that a large part of the voltage drop between the lead or leads through which current is generated, and case 110, occurs across the lungs, rather than in a vicinity of case 110.

When pacemaker 102 makes impedance measurements, there are several ways of making the measurements which are conventionally used to determine lung impedance. For example, pacemaker 102 may generate a given current through one of the leads, and measure a resulting voltage on the same or a different one of the leads. Alternatively, pacemaker 102 may apply a given voltage to one of the leads, or given voltages to each of the leads, and measure the resulting currents. Alternatively, pacemaker 102 may apply voltage and current related in a given way, for example a given voltage in series with a given resistance to limit current. Using a configuration that puts limits on both the current and the voltage may be advantageous for safety reasons.

In the preceding examples, each impedance measurement is found by dividing a voltage by a current, regardless of whether the voltage or the current or a combination of the two is fixed. Alternatively, pacemaker 102 makes an impedance measurement directly, without first finding a voltage and a current and dividing the voltage by the current. In describing FIGS. 2A through 6B, for convenience we will describe voltage being measured for given known currents, but it should be understood that the impedance measurements may be made in the ways mentioned above as well.

Figure 2A:
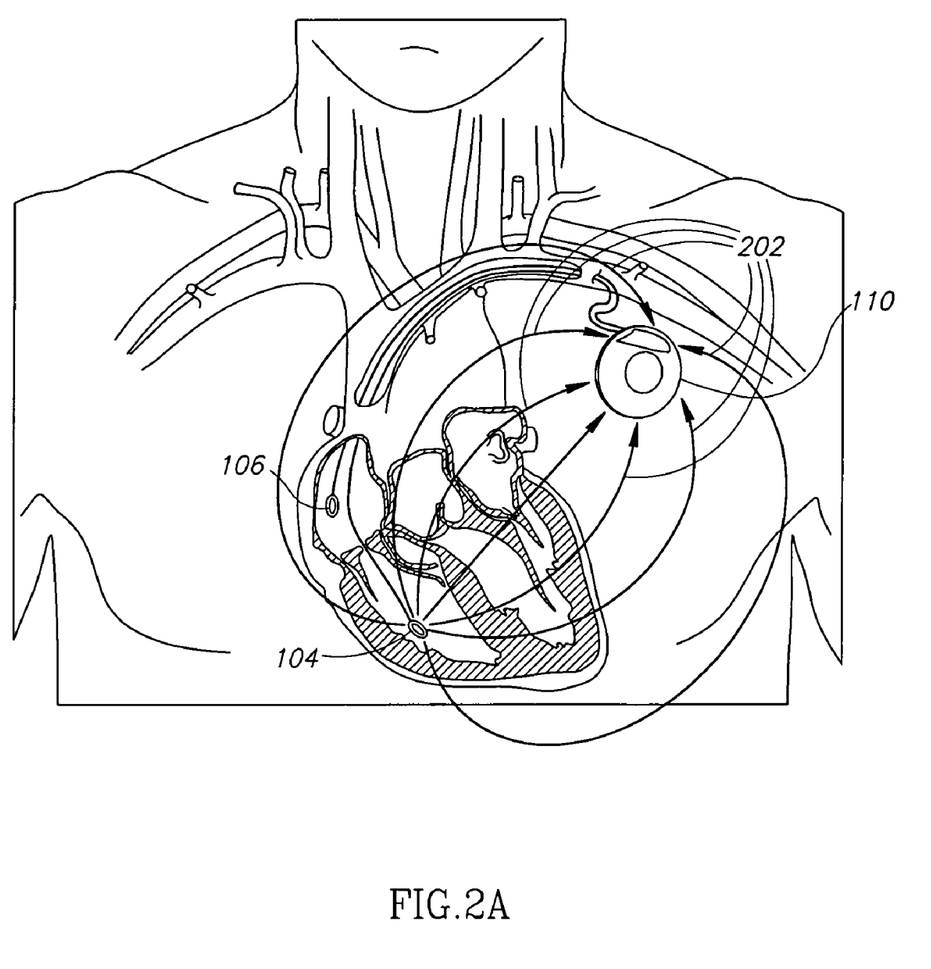
FIGS. 2A and 2B schematically show current paths in the chest, for current generated from the right ventricle and right atrium respectively, using the pacemaker shown in FIG. 1.
Figure 2B:
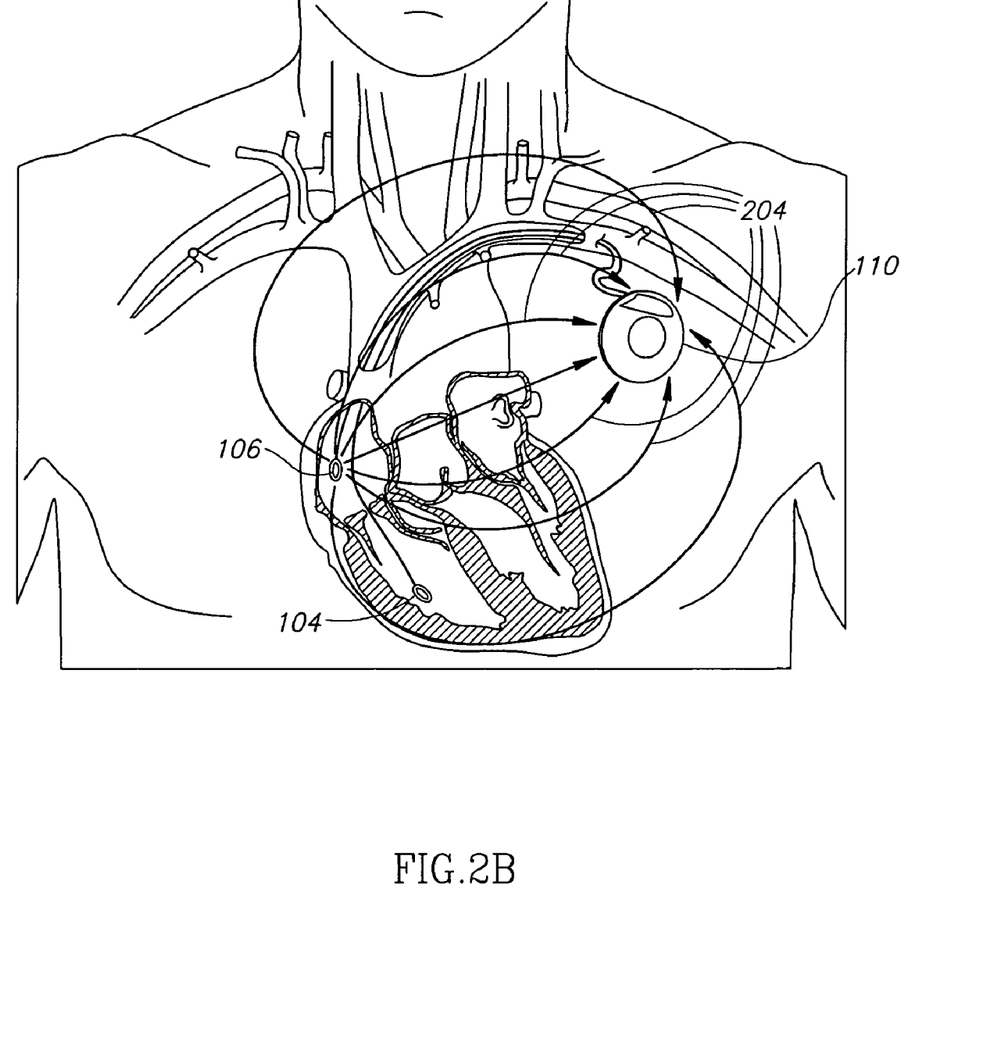

FIG. 2A schematically shows current paths 202 through the chest from lead 104 to case 110 of pacemaker 102, while FIG. 2B shows current paths 204 from lead 106 to case 110 of pacemaker 102. Because current paths 202 and 204 are distributed differently in the chest, measuring the voltage difference between each of the leads and the case, when current is generated through that lead, can provide information about the distribution of impedance in the chest. Alternatively or additionally, information about the distribution of impedance is provided by measuring the voltage on one lead when current is generated through the other lead. In some embodiments of the invention, currents having a known relationship are simultaneously passed through both leads 104 and 106 to case 110, to provide impedance information.

The currents and voltages used for providing bio-impedance measurements are configured so that they substantially do not interfere with vital functioning of the pacemaker. Any of various methods and devices known in the art may be used to appropriately configure the currents. For example, the currents may be configured so that their magnitudes are sufficiently low and/or their frequencies sufficiently high so that they do not interfere with the pacemaker functions. To substantially prevent "pacemaking" currents and voltages generated by the pacemaker from interfering with bio-impedance measurements, the measurements and pacemaker currents and voltages are optionally synchronized so that they are not simultaneous. Optionally, the impedance measurements and pacemaker currents and voltages do not interfere with each other because they are characterized by frequencies that are sufficiently different. Currents typically used for bio-impedance monitoring are less than about 10 mA, and are characterized by frequencies in a frequency range between 20 kHz and 200 kHz.

To measure excess fluid in the lungs associated with pulmonary edema, frequencies below 100 kHz are typically used, for the reasons explained above. At these lower frequencies, the impedance of the lungs and the rest of the chest is primarily resistive, and depends largely on the volume and distribution of low-resistivity blood and other extracellular fluid in the chest. Other body tissues, such as fat, muscle, and bone, as well as air in the lungs, have higher resistivities than blood and other extracellular fluids in the chest.

The relationship between an average impedance and degree of edema of each of the lungs, and voltage measured at each of leads 104 and 106 for given injected currents, may be modeled using suitable methods known in the art. For example, the relationship may be numerically calculated using a model of the spatial distribution and respective specific impedances of different body tissues in the chest, and a variable impedance for each of the lungs. The impedance of the lungs, in turn, may be related to a degree of lung edema, using a mathematical model and/or empirical data. P. Nopp, D. Harris, T. X. Zhao, and B. H. Brown describe a lung model suitable for the practice of the invention in an article titled "Model for the dielectric properties of human lung tissue against frequency and air content," *Medical and Biological Engineering and Computing* 35, 695-702 (1997), the disclosure of which is incorporated herein by reference.

Figure 3:
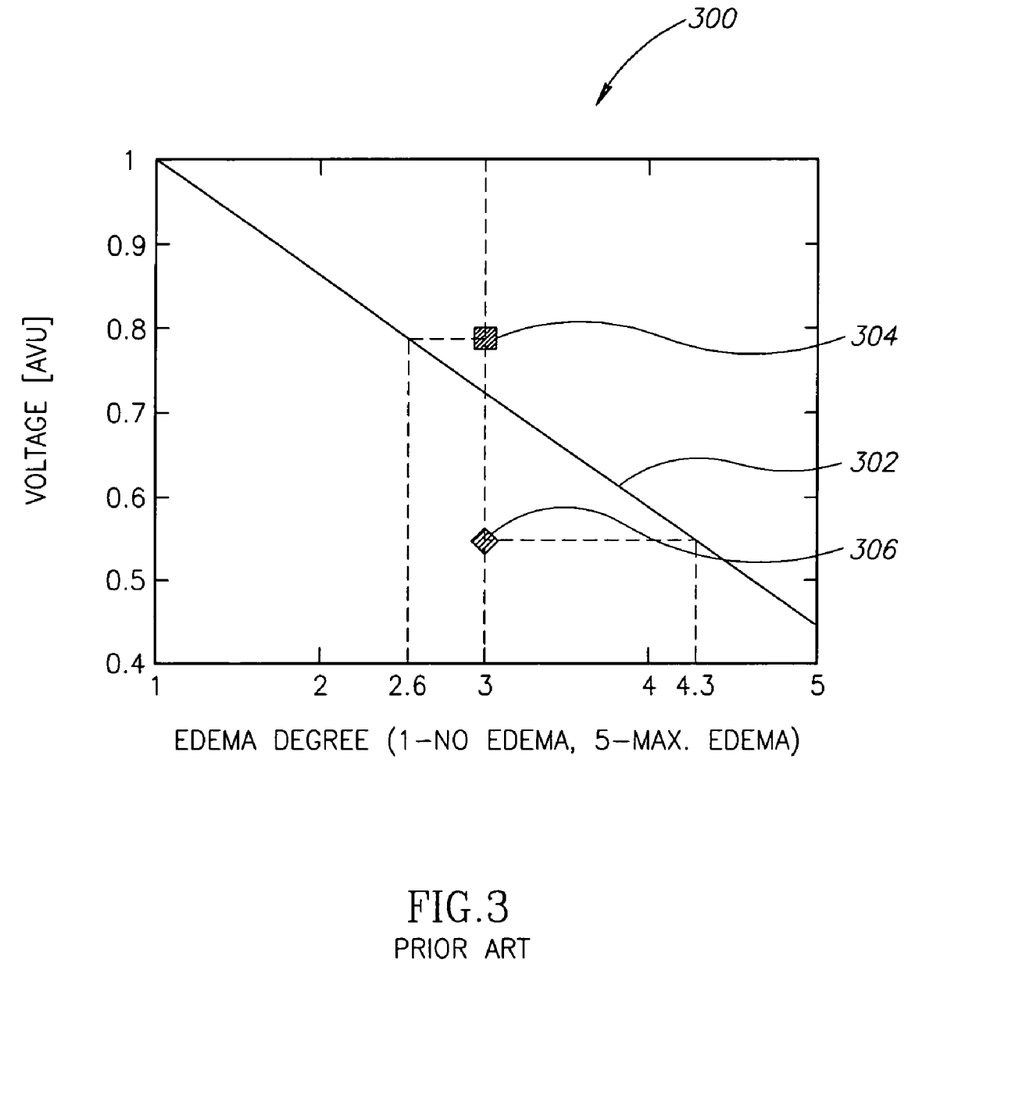
FIG. 3 shows a graph of lead voltage vs. degree of edema that indicates that prior art methods for determining pulmonary edema may provide edema estimates that are relatively inaccurate for situations of asymmetric pulmonary edema.

FIG. 3 shows a graph 300 of lead voltage vs. degree of pulmonary edema that indicates that conventional bio-impedance methods for determining degree of edema may provide estimates that are relatively inaccurate for a situation of asymmetric pulmonary edema. Degree of edema in FIG. 3 is defined by an arbitrary scale that ranges from degree 1, for the complete absence of edema and the mildest cases, to degree 5, for the most severe cases. In FIG. 3, a line 302 shows an expected voltage of lead 104 as a function of degree of pulmonary edema, assuming that current was generated by pacemaker 102 only between lead 104 and case 110. Line 302 was calculated using a numerical method such as described above, assigning a particular volume fraction of fluid for each degree of edema, assuming that the volume fraction of fluid is the same for both lungs and uniformly distributed within the volume of each lung. Graph 300 indicates that, under the assumptions of the calculation, voltage at only one lead, in the right ventricle, i.e. lead 104, can provide useful information about a degree of a patient's pulmonary edema.

FIG. 3 also shows two points 304 and 306 indicating voltage calculated for lead 104 were the two lungs to have very different degrees of pulmonary edema. Voltage 304 corresponds to the left lung having edema of degree 1, and the right lung having edema of degree 5, while voltage 306 corresponds to the left lung having edema of degree 5, and the right lung having edema of degree 1. Although in both cases the average degree of pulmonary edema in the two lungs is degree 3, the expected voltage at lead 104 is very different in the two cases, and also different from the expected voltage at lead 104 for symmetric pulmonary edema of degree 3, i.e. line 302. For the case (point 304) for which the right lung has edema of degree 5, the voltage on lead 104 indicates an average edema of degree 2.6, while for the case (point 306) for which the left lung has edema of degree 5, the voltage on lead 104 indicates an average edema of degree 4.3. Nearly two degrees of edema separate the indicated average level of edema in the two cases. The graph clearly indicates that for substantially asymmetric (unilateral) lung edema, conventional bio-impedance measurement using pacemaker leads are generally not reliable.

Figure 4:
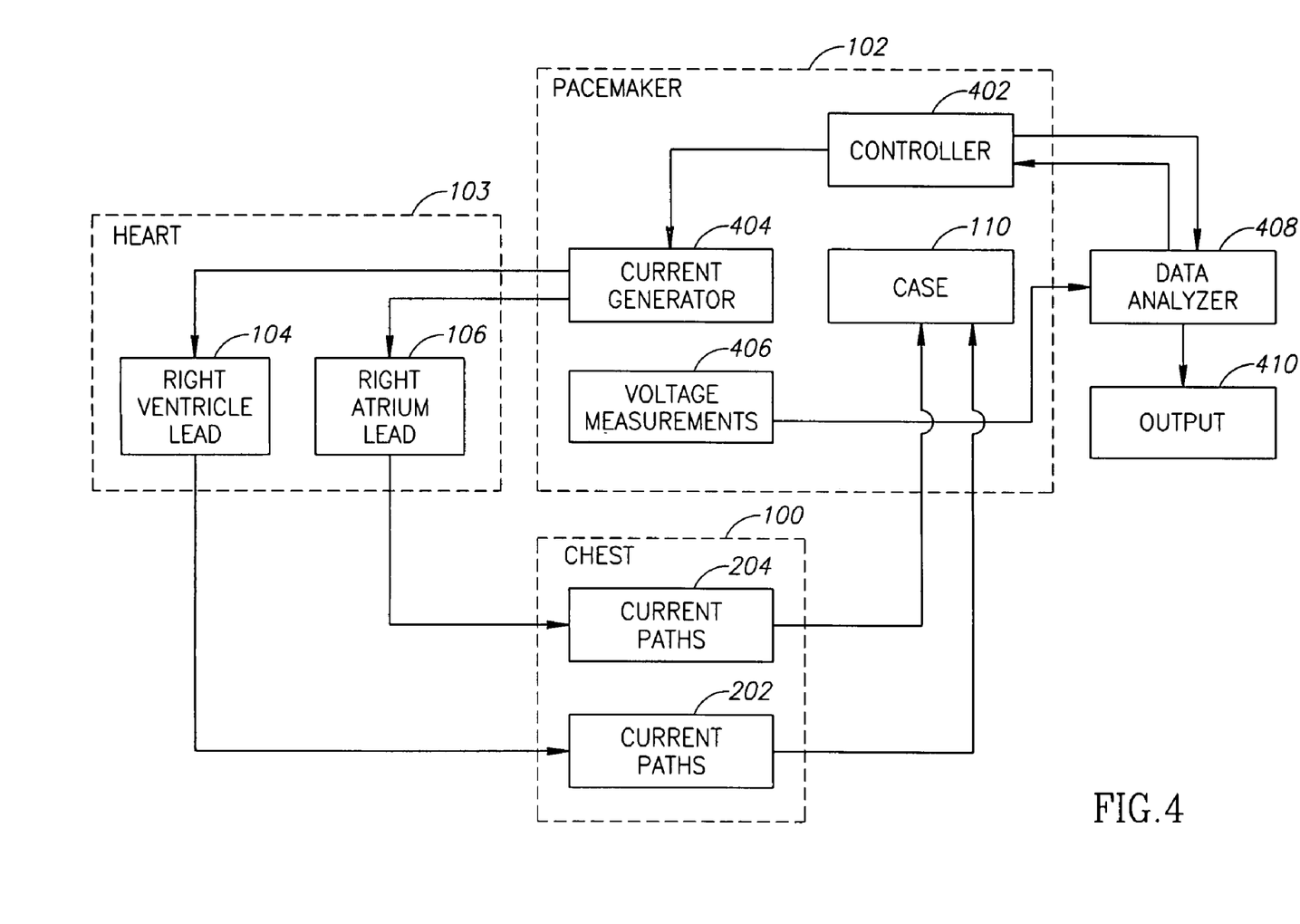
FIG. 4 shows a block diagram of the components of a bio-impedance system using an implanted pacemaker, according to an exemplary embodiment of the invention.

FIG. 4 is a block diagram, showing the relationship between different components of pacemaker 102, heart 103, and chest 100. Pacemaker 102 has a controller 402, which controls the timing, amplitude (optionally including phase), and optionally the frequency of current generated by a current generator 404, and injected through each of leads 104 and 106 (in FIG. 1) in the right ventricle and right atrium respectively, in heart 103. Optionally, controller 402 controls both the pacemaking and bio-impedance functions of pacemaker 102, and current generator 404 generates current for both purposes. Controller 402 optionally limits the bio-impedance measuring currents to time intervals in the cardiac cycle when no current is being generated for purposes of pacemaking. In some embodiments of the invention, parts of controller 402, or some of the functions of controller 402, are located outside the body, for example in a computer, and communicate with the pacemaker by, for example, a wireless method of communication.

Current may be generated through leads 104 and 106 sequentially, or simultaneously through both leads. When generated simultaneously, impedance measurements are made for at least two different ratios between the injected currents in order to provide at least two impedance measurements, but in different ratios for making different impedance measurements. Current generated through lead 104 goes through chest 100 along paths 202 (in FIG. 2A), to case 110, while current generated through lead 106 goes through chest 100 along paths 204 (in FIG. 2B). For current generated through only one of the leads at a time, paths 202 and paths 204 each include the entire chest, but with different distributions of current in the chest. If current is generated simultaneously through both leads, a resulting current pattern is generally a linear superposition of the current pattern from each lead by itself.

Current generator 404 sends voltage measurements 406 for each of the two leads, relative to the voltage of case 110, to a data analyzer 408, either directly, or through controller 402.

Data analyzer 408 is optionally housed in pacemaker 102, for example as part of controller 402. Alternatively, data analyzer 408 is located outside the body, and optionally communicates with pacemaker 102 by a wireless method of communication. Although the pacemaker could be connected to an external data analyzer by wires, any wires extending from the pacemaker to the outside of the body may increase the risk of infection. Even if data analyzer 408 is housed in pacemaker 102, a communications link to the outside of the body, preferably a wireless link, is optionally used to communicate output of the data analysis, for example estimates of the lung impedances, as well as to receive instructions, for example instructions to initiate impedance measurements.

In some embodiments of the invention, controller 402 controls current generator 404 to make at least two separate impedance measurements, generating current and/or measuring voltage using different leads, or using the leads in different ways, for each impedance measurement. Optionally, current generator 404 makes voltage measurements using only one lead for each impedance measurement, for example only the lead through which current is being generated. Alternatively, for at least one of the impedance measurements, current generator 404 also measures the voltage of one of the leads through which current is not being generated. In some embodiments of the invention, current is generated through a same one of the leads for both impedance measurements, and the two impedance measurements are distinguished by using different leads for the two voltage measurements.

In some embodiments of the invention, current is simultaneously generated through both leads, for each impedance measurement, but with different ratios of amplitude and/or different relative phases for different impedance measurements. In general, voltage may be measured on a same one of the leads or on a different one of the leads during each impedance measurement. In some embodiments, voltage is measured on both of the leads during each impedance measurement, and a weighted average is taken of the two voltages, optionally using a different weighting for each of the impedance measurements.

In some embodiments of the invention, the different impedance measurements are made at different times. Alternatively or additionally, different impedance measurements are distinguished by being made at different frequencies.

In some embodiments of the invention, only a single impedance measurement is made, using a voltage on one lead that is due at least partly to a current generated into the other lead.

Data analyzer 408 uses the voltage measurements and the values of the generated currents to calculate output 410 relating to pulmonary edema. For example, output 410 comprises estimates of the impedance of each lung, and/or an evaluation of the degree of edema in each lung, and/or an evaluation of whether the edema is getting worse in one or both of the lungs. Alternatively, output 410 only includes an estimate of the impedance or degree of edema of one lung, for example if the patient is known to have severe edema only in one lung, which needs to be monitored. However, since the method of calculating the lung impedance makes it easy to calculate the impedance of each lung, and in many patients it is important to monitor both lungs for edema, it is usually advantageous to include estimates for each lung in output 410.

Optionally, data analyzer 408 also communicates with controller 402, for example in order to find out from controller 402 what currents were being generated during the time that the voltage measurements were made, or to tell controller 402 what currents to generate. Data analyzer 408 may be a general purpose computer, particularly if data analyzer 408 is located outside the body. Alternatively, data analyzer 408, and optionally controller 402 as well, comprises specialized electronic circuitry adapted for the functions it performs, for example any suitable ASIC or generalized chip.

Figure 5:
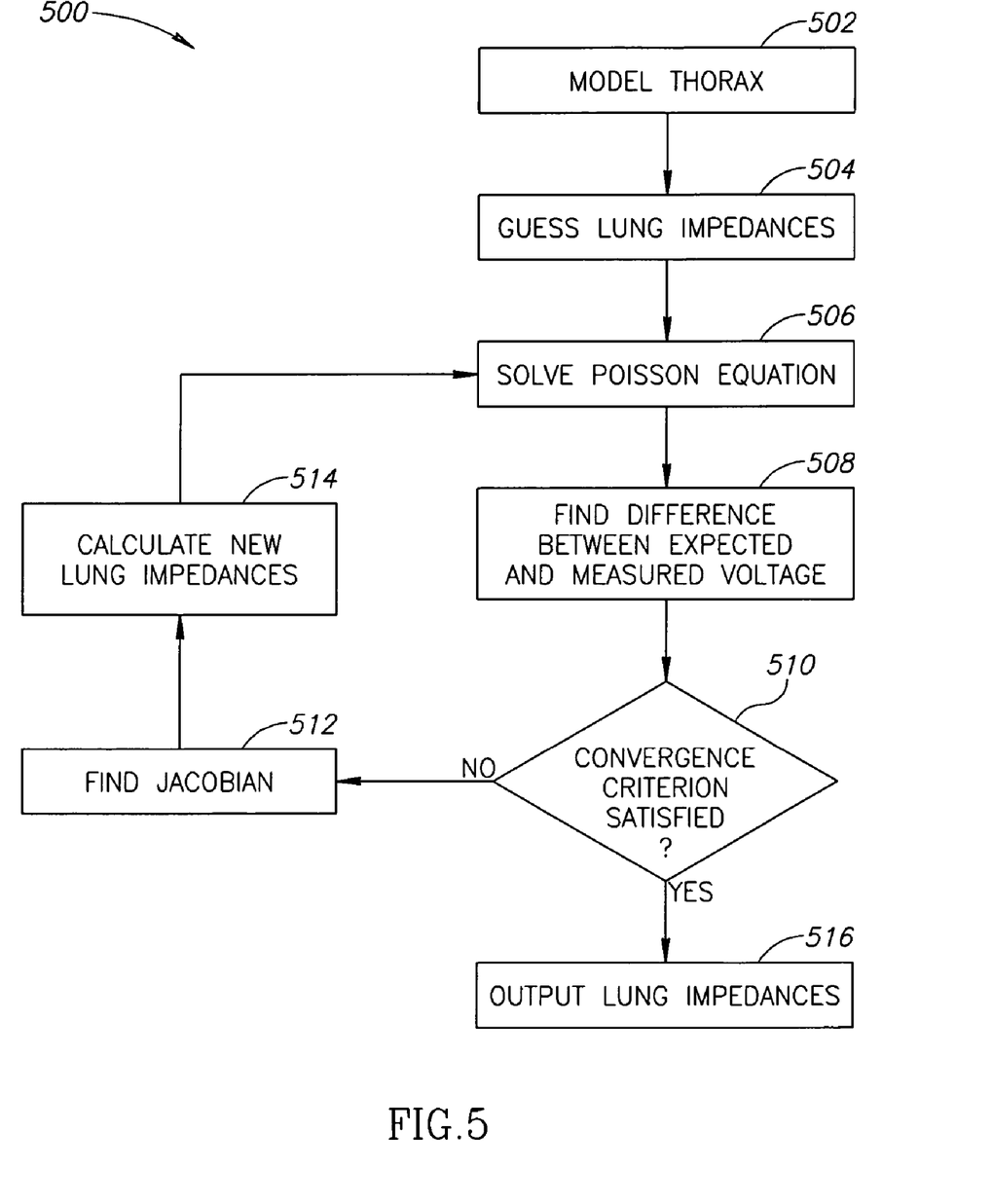
FIG. 5 shows a flowchart for a method of calculating left and right lung resistivity, according to an exemplary embodiment of the invention.

FIG. 5 shows a flowchart 500 for a method of analyzing the data used by data analyzer 408, in an exemplary embodiment of the invention. The method is optionally an iterative parameter optimization scheme based on the second-order Newton-Raphson method, starting with initial guesses for lung impedances. Other methods may be used instead, for example methods described by T. J. Yorkey et al, "Comparing reconstruction algorithms for electrical impedance tomography," IEEE Trans. Biomed. Eng. 34, 843-852 (1987), or sensitivity, back-projection, and direct-sensitivity methods. Suitable methods are reviewed by J. P. Morucci and P. M. Marsili, "Bioelectrical impedance techniques in medicine, Part III: Impedance imaging, Second Section: Reconstruction algorithms," Crit. Rev. Biomed. Eng. 24, 599-654 (1996). The disclosures of all these publications are incorporated herein by reference. However, parameter optimization techniques have a potential advantage of allowing reconstruction of lung impedances even when the initial guesses are not very close to the actual lung impedances.

At 502, a model of thorax impedance is created for the patient being examined. The model is, for example, a three-dimensional model describing the boundaries of the different types of tissue in the thorax, including blood, lungs, heart muscle, skeletal muscle, bone, fat, and skin. The boundaries of the different types of tissue are determined, for example, by using a three-dimensional medical image, such as an MRI or CAT scan, of the patient, or by using a standard model of a human thorax based on other subjects, optionally similar to the patient in one or more of height, weight, body build, chest measurement, body mass index (BMI), body surface area (BSA), and sex. A specific impedance is assigned to each tissue, other than the lungs. The assignment of lung impedance is described below. Optionally, the impedances assigned to each tissue are purely resistive. This may be done, for example, if the impedance measurements are to be made at relatively low frequencies, below 100 kHz, because only the resistive parts of the lung impedances are of interest. In general, the specific impedances of body tissues may be frequency dependent, and tissue impedances are assigned that are appropriate for the frequency at which the impedance measurements are to be made.

The model optionally assigns a specific impedance, or resistivity, to each volume element (voxel) in a Cartesian grid covering the thorax, or to each element in a more general polyhedral grid, for example a grid in which many grid points are located at the boundaries between different types of tissue, and at the surface of the leads and the pacemaker case.

Optionally, the choice of grid used in the model depends on the numerical method that is used to solve the Poisson equation, as will be described below. For example, a Cartesian grid may be chosen if a finite difference method is to be used, while a more general grid may be chosen if a finite element or finite volume method is to be used.

At 504, initial guesses are made for the left lung impedance, and the right lung impedance, at the frequency at which impedance measurements are to be made. The initial guesses are based, for example, on typical values of lung impedance for healthy subjects, and/or on values of lung impedance calculated for this patient in an earlier bio-impedance measurement, and/or on typical values of lung impedance for patients with the same degree of pulmonary edema that this patient is believed to have, based, at least in part, on other diagnostic methods.

At 506, a Poisson equation, $$\nabla \cdot \left(\frac{1}{\rho} \nabla \psi\right) = -I_v$$

is solved to find the electric potential $\psi$ as a function of position in the thorax, in particular at the lead or leads where the voltage is measured. Here $\rho$ is the specific impedance of the thorax as a function of position in the thorax, assigned at 502 and 504, as described above, and $I_v$ is zero except at the surfaces of any lead through which current is being generated, and at the surface of case 110, where $I_v$ is a delta-function times the current density normal to that point on the surface.

Since the leads and the case are good conductors, the potential has a constant value everywhere on the surface of the case, and has a constant value, in general different from the potential at the case, everywhere on the surface of lead 104, and a third constant value everywhere on the surface of lead 106, generally different from the potentials at the case and at lead 104. Poisson's equation is optionally solved subject to a boundary condition that each of these surfaces is an equipotential. Optionally, another boundary condition is that the current integrated over the surface of each lead is equal to the current generated through that lead. Optionally, another boundary condition is that the current density integrated over the surface of the case is equal to the negative of the current going into the case, which is the total current generated through the leads. Neumann boundary conditions, specifying a normal electric field or zero, are optionally chosen for the vertical and radial surfaces of the thorax model, since no current flows outside the body, and very little current will extend past the vertical limits of the thorax model if they are far enough away from the heart, lungs, and pacemaker.

Since exact solutions to the Poisson equation generally do not exist for a complicated geometry such as that of the thorax, numerical methods may be used. Any known numerical method of solving partial differential equations is optionally used, for example the finite difference method, the finite element method, the finite boundary element method, or the finite volume method. These methods generally provide values of the potential $\psi$ at each point on a grid, and various interpolation methods may be used to find $\psi$ at other points. Numerical methods in which arbitrary grid points (rather than Cartesian grid points) can be used may have a potential advantage, since grid points may be chosen to cover the surfaces of the leads and the pacemaker case fairly densely, while fewer grid points are used inside large volumes with uniform resistivity.

The solution found at 506 provides a potential $\psi_s$ of each lead, relative to the pacemaker case. Optionally, these potentials are found first for a situation of current generated through one lead, and then for a situation of current generated through the other lead, or for two different ratios of current generated through the two leads, if measurements of voltage are made for two different situations of current generation. Thus, up to four independent potentials $\psi_s$ may be found, corresponding to voltage measured on each of the two leads, with current generated through each of the two leads. Alternatively, only two or three of these potentials $\psi_s$ are found. The independent potentials $\psi_s$ found by solving the Poisson equation may be symbolized by a vector $\vec{\psi}_s$, while the corresponding measured potentials $\psi_0$ are symbolized by a vector $\vec{\psi}_0$.

At 508, the difference vector $\vec{\psi}_s - \vec{\psi}_0$ between the calculated and measured potentials is found. At 510, the difference vector is examined to see whether it is small enough to satisfy a convergence criterion. The convergence criterion may be satisfied on any of the components of the vector or any combination of the components, but typically the convergence criterion is only satisfied if all of the components are sufficiently small. For example, the convergence criterion requires that the L2 norm of $\vec{\psi}_s - \vec{\psi}_0$ (the Euclidean distance between $\vec{\psi}_s$ and $\vec{\psi}_0$) be smaller than a given value, or smaller than a given fraction of the magnitude of $\vec{\psi}_s$, such as $10^{-2}$ of the magnitude, or $10^{-3}$ of the magnitude, or $10^{-6}$ of the magnitude, or $10^{-10}$ of the magnitude. Simulations show that the L2 norm of $\vec{\psi}_s - \vec{\psi}_0$ typically converges to within about $10^{-10}$ of the magnitude of $\vec{\psi}_s$ in about 10 iterations. If the convergence criterion is too stringent, for example less than the round-off error of the computer, it may never be met, or the computation may take an unnecessarily long time. If the convergence criterion is not stringent enough, the output values for lung resistivity may not be very accurate, and the method may not evaluate the degree of pulmonary edema very accurately.

For clarity of exposition, we first describe an embodiment of the invention where only two components of $\vec{\psi}_s$ and $\vec{\psi}_0$ are found, and where each lung impedance is assumed to be uniform, and all other specific impedances in the thorax are assumed to have fixed values. Later we will describe other embodiments. The two lung impedances $\rho_{left}$ and $\rho_{right}$ may be symbolized by a two-component vector $\vec{\rho}_k$, where k is an iteration number. The vector $\vec{\psi}_s$ of potentials found by solving the Poisson equation depends on the vector of lung impedances $\vec{\rho}_k$. The vector $\vec{\psi}_s$ may therefore be written as $\vec{\psi}_s(\vec{\rho}_k)$.

At 512, the Jacobian matrix $\mathcal{J}_k$ is found. This matrix, which is a 2×2 matrix for the embodiment we are considering, is defined by $$\mathcal{J}_k = \frac{\partial \vec{\psi}_s(\vec{\rho}_k)}{\partial \vec{\rho}_k}$$

The Jacobian matrix may be found, for example, by solving Poisson's equation for slightly different values of the lung impedances than were used previously, and seeing how this affects the potentials $\vec{\psi}_s$, preferably using a convergence criterion that is small relative to the change in $\vec{\psi}_s$. Optionally, the Jacobian matrix is found for each iteration. Alternatively, for example to save computation time, the Jacobian matrix is only found if the lung impedances have changed by a sufficiently large amount since the last time the Jacobian matrix was found, such that the Jacobian matrix is expected to change significantly. The Jacobian matrix may be calculated at any time in the loop of the flowchart consisting of 506, 508, 510, 512, and 514, but for clarity of exposition we describe the calculation of the Jacobian at 512 in the flowchart.

At 514, a new vector $\vec{\rho}_{k+1}$ for the lung impedances is found by using the equation $$\vec{\rho}_{k+1} = \vec{\rho}_k - (\mathfrak{J}_k^T(\vec{\rho}_k)\mathfrak{J}_k(\vec{\rho}_k))^{-1}\mathfrak{J}_k^T(\vec{\rho}_k)(\vec{\psi}_s(\vec{\rho}_k) - \vec{\psi}_0)$$

Then the Poisson equation is solved again at 506, as described above, using the new values of lung impedance, and the loop repeats until the convergence criterion is met at 510. Optionally, if the convergence criterion is not satisfied after a certain number of iterations, then the program exits and indicates a failure to converge.

When the convergence criterion is met at 510, the final values for lung impedance are output at 516. Alternatively, only one of the values of lung impedance is output at 516, for example if only one of the lungs is being examined for edema, or only an average value for the two lungs is output at 516.

Figure 6A:
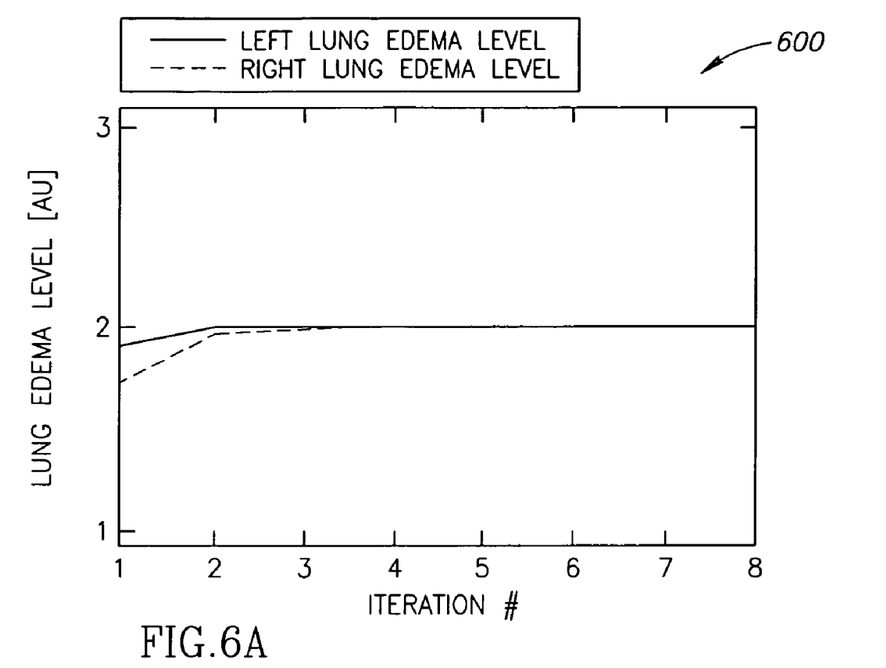
FIGS. 6A and 6B show plots of the convergence of the estimated left lung and right lung resistivity, for two different simulated cases, according to an exemplary embodiment of the invention.
Figure 6B:
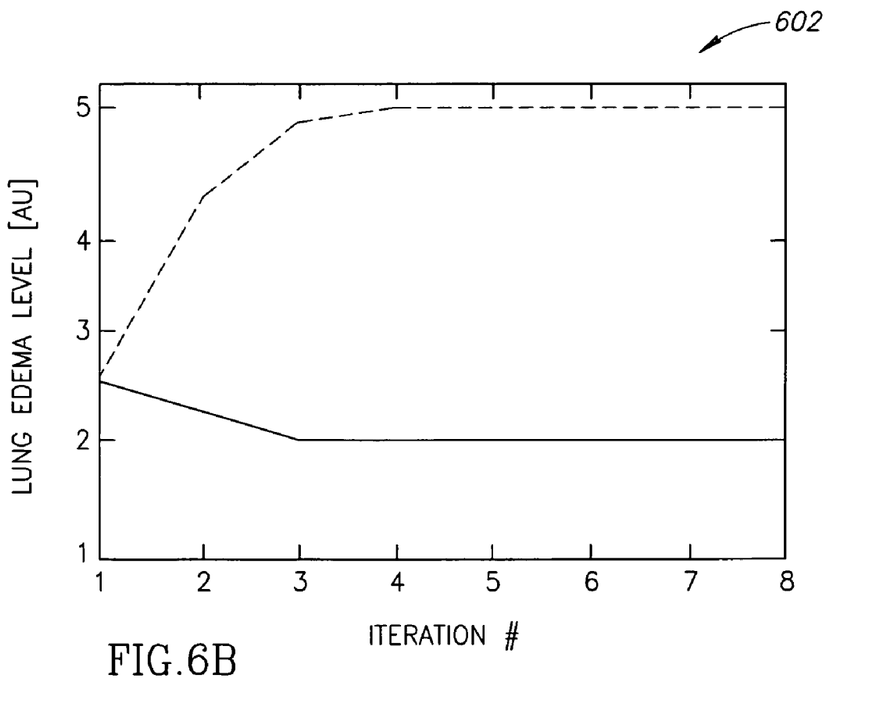

FIGS. 6A and 6B shows plots 600 and 602 of the calculated degree of pulmonary edema (based on lung impedance) vs. iteration number k, for two simulated patients. In plot 600, the patient has the same degree of pulmonary edema in both lungs. In plot 602, the patient has very different degrees of pulmonary edema in each lung. In both cases, the calculated lung impedance (and hence the degree of pulmonary edema) converges in only a few iterations for both lungs.

In some embodiments of the invention, three or four different potentials are measured and calculated, so $\vec{\psi}_s$ and $\vec{\psi}_0$ have three or four components instead of only two components. In some such embodiments, the number of variable impedance parameters is equal to the number of potentials, so the vector $\vec{\rho}_k$ of impedances has the same number of components as $\vec{\psi}_s$ and $\vec{\psi}_0$. For example, it may be useful to include an effective blood resistivity as a varying impedance parameter, together with the left and right lung impedances. Although the resistivity of blood may not really vary significantly, treating it as a free parameter may be used to simulate changes in intravascular volume. Patients with pulmonary edema often also have changes in intravascular volume, which can affect the impedance of the thorax, and may produce misleading conclusions about changes in lung impedance. Including the effective blood resistivity as a free parameter may produce more accurate values of lung impedance for these patients. It may also be useful to divide up one or both lungs into two or more regions, and treat the specific impedance of each region as an independent parameter. Although resistivity tends to be fairly uniform throughout each lung in the early stages of pulmonary edema, more fluid may accumulate near the bottom of the lungs in later stages, and dividing each lung into an upper and lower region, for example, for a total of four components of lung impedance, may produce more accurate evaluations of pulmonary edema in patients with later stage disease.

When the number of components of the impedance vector $\vec{\rho}_k$ is equal to the number of components of the potentials $\vec{\psi}_s$ and $\vec{\psi}_0$, then the iterative method described above for two components may still be used, the only difference being that the vectors have three or four components instead of two components, and the Jacobian matrix is 3×3 or 4×4.

In some embodiments of the invention, more components of potential are measured and calculated, than there are free parameters of the impedance. In this case, the problem of calculating the lung impedances from the measured potentials is over-determined, and may be solved using any of the standard methods used for solving over-determined problems, for example the least squares method, described by D. S. Watkins, *Fundamentals of Matrix Computations* (Wiley-Interscience, 2002), the disclosure of which is incorporated herein by reference. The redundancy provided by the extra potential measurements may result in more accurate values for the lung impedances, and also provides a check on the self-consistency of the data and the model.

It should be noted that even if the model used for the thorax does not result in output values for the lung impedances that are very accurate absolutely, the model may still provide an accurate assessment of whether the lung impedances have changed since the last time the patient was tested, and in what direction it has changed. For purposes of treating a patient with pulmonary edema, knowing whether and to what extent the lung impedances have changed may be more important than knowing their values absolutely at a given time.

The disclosures of all publications cited here are incorporated herein by reference.

The invention has been described in the context of the best mode for carrying it out. It should be understood that not all features shown in the drawings or described in the associated text may be present in an actual device, in accordance with some embodiments of the invention. Furthermore, variations on the method and apparatus shown are included within the scope of the invention, which is limited only by the claims. Also, features of one embodiment may be provided in conjunction with features of a different embodiment of the invention. As used herein, the terms "have", "include" and "comprise" or their conjugates mean "including but not limited to." As used in the claims, "pacemaker" also includes defibrillators, and "impedance," when referring to a lung, means "specific impedance."

The invention claimed is:

1. A method of determining a specific impedance of tissue of at least one of two lungs of a patient having an implanted pacemaker that comprises first and second leads and a case, the method comprising:
   a) using the first and second leads and the case to acquire at least a first and a second impedance measurement responsive to impedance of the patient's chest, said first and second impedance measurements being at least partially independent; and
   b) determining the specific impedance of tissue of at least a first one of the patient's lungs substantially independently of specific impedance of tissue of the second one of the patient's lungs, such that Poisson's equation for a model of the chest has a solution consistent with the at least two impedance measurements.

2. A method according to claim 1, wherein the model of the chest treats the specific impedances of tissue of the two lungs as two independent variables.

3. A method according to claim 1, wherein, for each impedance measurement, a different configuration of the first and second leads is used than is used for any other of the impedance measurements, for generating current or for measuring voltage or for both.

4. A method according to claim 3, wherein, for the first and second impedance measurements, the current is generated only between the case and one of the leads, the same lead for both the first and second impedance measurements, and the voltage involves only a potential difference between the case and one of the leads, a different one for the first impedance measurement than for the second impedance measurement.

5. A method according to claim 1, wherein determining the specific impedance of tissue of at least one lung comprises determining the specific impedances of tissue of both lungs.

6. A method according to claim 5, wherein the impedance measurements also comprise a third impedance measurement.

7. A method according to claim 6, also including determining a third parameter of the patient's thorax, in addition to the two specific impedances of tissue of the lungs.

8. A method according to claim 7, wherein the third parameter comprises an intravascular volume of the patient's thorax.

9. A method according to claim 6, wherein a least squares method is used to find a fit of the two specific impedances of tissue of the lungs to the at least three impedance measurements.

10. A method according to claim 5, wherein determining the specific impedances of tissue of the lungs comprises:
   a) making an initial guess for values of the specific impedances;
   b) calculating expected impedance measurements for said values of the specific impedances;
   c) correcting values of the specific impedances according to a difference between measured and expected values for the impedance measurements; and
   d) repeating (b) and (c) until a convergence criterion is satisfied.

11. A method according to claim 10, wherein calculating expected impedance measurements comprises using one or more of a finite element method, a finite difference method, a finite boundary element method, and a finite volume method.

12. A method according to claim 1, wherein determining the specific impedance of tissue of at least one lung comprises determining the specific impedance of tissue of the lung responsive to a solution of equations that satisfy constraints defined by the first and second impedance measurements, for a model of the chest with two specific impedances of lung tissue as unknowns.

13. A method according to claim 1, wherein the case is implanted on a side of the patient's chest opposite to the side of the first lung.

14. A method according to claim 1, wherein one of the leads is implanted in a right ventricle of the patient.

15. A method according to claim 1, wherein one of the leads is implanted in a right atrium of the patient.

16. A method according to claim 1, wherein one of the leads is implanted in a left ventricle coronary vein of the patient.

17. A method according to claim 1, wherein the case is implanted in a left pre-pectoral position.

18. A method according to claim 1, wherein the case is implanted in a right pre-pectoral position.

19. A method of determining a specific impedance of tissue of at least one lung in a chest of a patient, comprising:
   a) generating one or more currents, each between a pacemaker case implanted in the chest, and at least one of a first lead and a second lead implanted at different locations in a heart of the patient;
   b) measuring one or more voltages, each involving a potential difference between at least one of the first and second leads and the case, including at least a first voltage due at least in part to at least a portion of the current which is generated between the other one of the first and second leads and the case; and
   c) calculating the specific impedance of tissue of at least one lung only from the one or more currents and the one or more voltages, including at least the first voltage.

20. A pacemaker for bio-impedance measurements, comprising:
   a) a case adapted for implanting in the chest;
   b) a first lead adapted for implanting at a location in the heart;
   c) a second lead adapted for implanting at a different location in the heart;
   d) a bio-impedance system, adapted to make impedance measurements comprising at least a first and a second impedance measurement, using voltage differences between the case and the first and second leads; and
   e) a data analyzer, adapted to determine a specific impedance of tissue of at least a first one of the lungs, substantially independently of specific impedance of tissue of the other lung, such that Poisson's equation for a model of the chest has a solution consistent with the at least two impedance measurements.

21. A method of determining specific impedances of tissue of at least three portions of two lungs of a patient having an implanted pacemaker that comprises first and second leads and a case, the method comprising:
   a) using the first and second leads and the case to acquire at least a first, a second and a third impedance measurement responsive to impedance of the patient's chest that are at least partially independent; and
   b) using the impedance measurements to determine the specific impedance of tissue of at least three portions of the lungs of the patient, including at least one portion of one of the patient's lungs, and at least two portions of the other one of the patient's lungs, substantially independently of each other.

* * * * *